(12) United States Patent
Marcoux

(10) Patent No.: US 9,154,888 B2
(45) Date of Patent: Oct. 6, 2015

(54) SYSTEM AND METHOD FOR HEARING AID APPRAISAL AND SELECTION

(75) Inventor: André M. Marcoux, L'Original (CA)

(73) Assignee: Eastern Ontario Audiology Consultants, L'Original (CA)

(*) Notice: Subject to any disclaimer, the term of this patent is extended or adjusted under 35 U.S.C. 154(b) by 401 days.

(21) Appl. No.: 13/533,809

(22) Filed: Jun. 26, 2012

(65) Prior Publication Data

US 2013/0343583 A1 Dec. 26, 2013

(51) Int. Cl.
*H04R 25/00* (2006.01)
*H04R 29/00* (2006.01)

(52) U.S. Cl.
CPC ............... *H04R 25/50* (2013.01); *H04R 25/70* (2013.01); *H04R 29/00* (2013.01); *H04R 2225/41* (2013.01)

(58) Field of Classification Search
CPC ........ G01H 3/14; H04R 29/00; H04R 29/001; H04R 29/004; H04R 25/70; H04R 25/505; H04R 2225/41
USPC .......................... 381/56, 58, 314, 60; 73/585
See application file for complete search history.

(56) References Cited

U.S. PATENT DOCUMENTS

| 5,923,764 A * | 7/1999 | Shennib .......................... 381/60 |
| 6,322,521 B1 * | 11/2001 | Hou ............................... 600/559 |
| 7,027,606 B2 * | 4/2006 | D'Agri ........................ 381/312 |
| 7,181,297 B1 | 2/2007 | Pluvinage et al. |
| 7,854,704 B2 | 12/2010 | Givens et al. |
| 2002/0068986 A1 * | 6/2002 | Mouline ........................ 700/94 |
| 2008/0165978 A1 * | 7/2008 | Cronin et al. ................... 381/58 |
| 2010/0111338 A1 * | 5/2010 | Ypma et al. ................... 381/314 |
| 2011/0200214 A1 * | 8/2011 | Knox et al. .................... 381/314 |
| 2011/0257994 A1 * | 10/2011 | Givens et al. ..................... 705/2 |

* cited by examiner

*Primary Examiner* — Matthew Eason
*Assistant Examiner* — Sean H Nguyen
(74) *Attorney, Agent, or Firm* — Sean D. Burdick

(57) ABSTRACT

The selection of hearing aids can be based on many factors which are beyond a simple compensation for the hearing impairment of the user. The process of selecting hearing aids can be time consuming and resource intensive. By rapidly and effectively providing the necessary context to hearing-impaired individuals to evaluate the benefit provided by various hearing aids, without the traditional time consuming fitting trial, the purchase of a device can be expedited and provide the necessary correction to negate the effects of auditory deprivation. A system an method for enabling improved hearing aid appraisal and selection processes is provided.

20 Claims, 6 Drawing Sheets

SYSTEM AND METHOD FOR HEARING AID APPRAISAL AND SELECTION

TECHNICAL FIELD

The present disclosure relates to hearing aids and in particular to appraisal and selection of hearing aids for patients.

BACKGROUND

It has been well documented that 3 in 10 adults over the age of 60 will acquire hearing loss, most of which will be diagnosed with presbycusis, an irreversible deterioration of the sensorineural aspects of the auditory system. There are also other etiologies of hearing loss, such as genetic congenital manifestations and noise-induced trauma, which can affect individuals in diverse age groups. The most practical and widely-used treatment for presbycusis and other forms of sensorineural hearing loss is with hearing aids; personal devices which can restore the loss of auditory sensation measured during one's audiological assessment.

Considerable research and development efforts have been set forward to provide hearing aids which precisely correct an individual's loss of hearing without discomfort or inconvenience. Despite the investment in research and development, patients may remain dissatisfied with the results provided by hearing aids and/or the lack of knowledge from those fitting these devices. Compounded to this possible poor performance are the elevated costs for this research and development which are passed along to the patients. As such, many patients are reticent to purchase hearing aids as they are unable to determine the cost/benefit ratio for the devices and will often postpone correction of hearing loss to their detriment. Prolonged auditory deprivation has been linked to loss of neural atrophy resulting in poor speech discrimination, social isolation and dementia in the elderly.

Currently the only means for a hearing-impaired individual to gauge benefit from hearing aids is by experiencing sound from the hearing aids themselves. Due to the time involved in this process, many individuals are unable to achieve their due diligence prior to purchasing these expensive devices, or may not trust the competencies of dispensers from retail outlets in selecting the best devices. As such, there is tremendous loss to follow-up and a low buy-in from hearing-impaired patients.

Accordingly, systems and methods that enable improved hearing aid appraisal and selection processes become highly desirable.

BRIEF DESCRIPTION OF THE DRAWINGS

Further features and advantages of the present disclosure will become apparent from the following detailed description, taken in combination with the appended drawings, in which.

It will be noted that throughout the appended drawings, like features are identified by like reference numerals.

DETAILED DESCRIPTION

Figure 1:
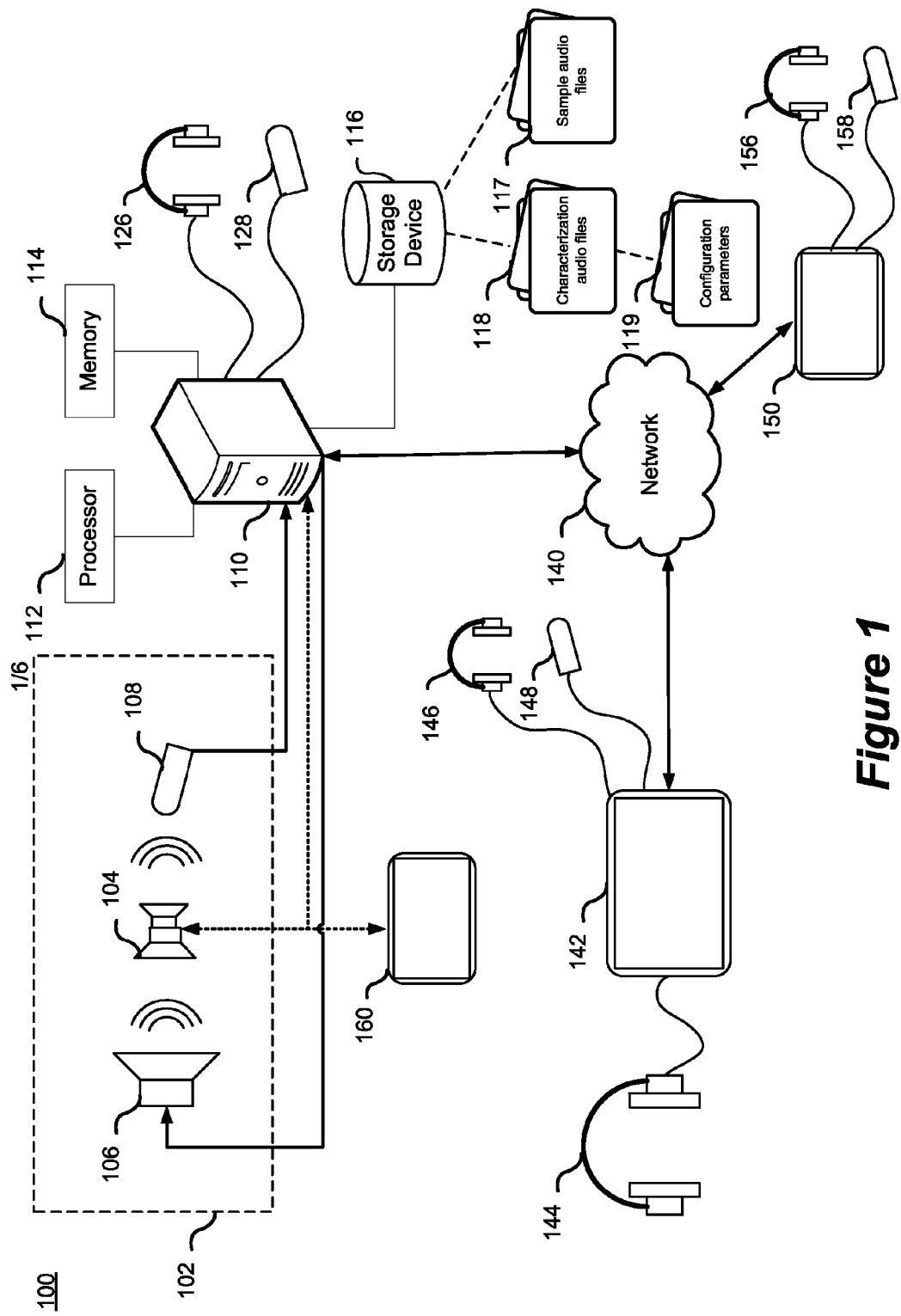
FIG. 1 shows a representation of a system for hearing aid appraisal and selection.

Embodiments are described below, by way of example only, with reference to FIGS. 1-6. It will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

In accordance with an aspect of the present disclosure there is provided a method, executable on one or more processors, of appraisal and selection of hearing aids, the method comprising: receiving a plurality of user parameters determined from audiometric parameters defining hear-ability of the user; determining one or more hearing aids, configurable to meet the requirements of the plurality of user parameters; determining one or more characterization audio files associated with the determined one or more hearing aids and associated source audio files from which the one or more characterization audio files were generated; and playing to the user through audio transducers coupled to a playback device the one or more characterization audio files and the associated source audio files.

In accordance with another aspect of the present disclosure there is provided a system of appraisal and selection of hearing aids, the system comprising: audio transducers; and a computing device coupled to the audio transducers, the computing device performing: receiving a plurality of characterization audio files each generated by recording an output from a respective hearing aid of a source file played through the respective hearing aid having been configured using a set of configuration parameters; playing to the user, through the audio transducers, each of the plurality of characterization audio files and associated source audio files; and receiving a preference selection of one or more of the plurality of characterization audio files to identify a hearing aid preference.

In accordance with yet another aspect of the present disclosure there is provided a computer readable memory containing instructions which when executed on one or more processor for providing appraisal and selection of hearing aids, the instructions comprising: receiving a plurality of user parameters determined from audiometric parameters defining hear-ability of the user; determining one or more hearing aids, configurable to meet the requirements of the plurality of user parameters; determining one or more characterization audio files associated with the determined one or more hearing aids and associated source audio files from which the one or more characterization audio files were generated; and playing to the user through audio transducers coupled to a playback device the one or more characterization audio files and the associated source audio files.

The selection of hearing aids can be based on many factors which are beyond a simple compensation for the hearing impairment of the user. The process of selecting hearing aids can be time consuming and resource intensive. By rapidly and effectively providing the necessary context to hearing-impaired individuals to evaluate the benefit provided by various hearing aids, without the traditional time consuming fitting trial, the purchase of a device can be expedited and provide the necessary correction to negate the effects of auditory deprivation.

FIG. 1 shows a system for hearing aid appraisal and selection. The system 100 provides the ability to generate characterization audio files of individual hearing aids and provide the audio files to a user in a graphical user interface so that a user may sample the different hearing aids without having to physically have them fitted to their ears. The characterization configuration 102 provides calibrated loudspeakers, 106, coupled to a characterization server 110 such as a computer, to output source audio files 117 to a single hearing aid or to a set of hearing aids 104. Calibrated microphones 108 receive the output of the hearing aid(s) 104 and the computer stores the characterization audio files 118. The microphones 108 may also be placed within a manikin designed to mimic the effects of the head, torso and outer ear on acoustic inputs, such as those delivered by the calibrated loudspeakers 106. The characterization audio files providing a sample of the audio improvement that may be provided by particular hearing aid device(s) 104. The characterization server 110, comprising at least a processor 112 and a memory 114, and coupled to a storage device 116 containing instructions and audio files and user and hearing aid configuration parameter information. The audio files and configuration parameter information may comprise source audio files 117, characterization audio files 118 and the configuration parameters 119 of each of the characterization audio files 118. The output of the hearing aid(s) 104 may be recorded for each source audio file 117 using different configuration parameters of the respective hearing aid(s) such as prescribed gain, compression or any processing feature or which can be activated within the hearing aid(s) by way of its programming software. Each hearing aid or set of hearing aids 104, may generate multiple characterization audio files 118 for each source file based upon the varying configuration options of the particular hearing aid(s) 104, which are activated using the hearing aids' proprietary software installed on the characterization server 100, or another computing device 160, and which communicated with the hearing aids 110, either in a hard-wired or wireless transmission using a compatible programming interface. The programming of the hearing aid and the playback of the source files may be automated for each hearing aid. The recording of the characterization audio files 118 within the characterization configuration 102 can be performed in a controlled environment so that the output between the hearing aids 104 is consistent and reproducible. The source audio file may be samples of audio environments or audio samples in which hearing impairments would be improved by a hearing aid. For example the source audio files may be based upon speech in a quiet environment, speech with various types of background; music in a quiet environment, and music with various types of background, etc.

A patient herein referred to as a user, can access the recorded characterization audio files 118 through a computing device 142 such as a tablet, smartphone, netbook, notebook, or personal computer. The computing device 142 is coupled to the characterization server 110, either through a wired or wireless network such as a local area network (LAN), or a wide area network (WAN) 140 for receiving the characterization files. The computing device 142 is coupled to a calibrated pair of headphone type audio transducers 144 for the user to hear the audio files. A pair of monitoring headphones 146 as well as a microphone 148 is used by the clinician to monitor the playback as well as to speak with the user wearing the headphone type audio transducer 144 to provide verbal context as required. Alternatively, the clinician may be able to interact with the user remotely by monitoring headphones 126 as well as a microphone 128 coupled to the characterization server 110 or similar interaction server, or by a computing device 150 having monitoring headphones 156 as well as a microphone 158 coupled via the network 150 to enable monitoring of client progress and facilitate direct communication. A graphical user interface is provided on the computing device 142 to allow the selection of characterization audio file 118 so that the user may sample the improvement of particular hearing aids 104 relative to the source audio files 117. The computer device 142, or the characterization server 110 may select the characterization files based upon user parameters, such as audiometric results and user requirements such as lifestyle, cost, and expected level of benefit. The configuration parameters 119 provide an association between the characterization audio files and the configuration parameters used to configure the hearing aid. The configuration parameters may be provided in a separate file or database or may be embedded in metadata of the audio files and in addition, a mapping may be provided between the particular hearing aid configuration parameters and provided user parameters. For example, a particular hearing impairment may require certain parameters to be configured such as gain, which may only be available on a subset of available hearing aids. Mapping of the user requirements to the configuration parameters can reduce the selection of possible hearing aids required for comparison by the user. The user can then sample the improvement of the particular hearing aid 104 by sampling audio files processed by the hearing aid 104 without having to try on the physical hearing aid 104. By removing the requirement to physically fit the hearing aids prior to their purchase, the appraisal and selection processes relating to hearing aids can be expedited and the adoption rate improved. The user may interact directly with the graphical user interface provided by the computing device 142, or the computing device may be operated by a clinician or technician to control playback and hearing aid selection.

The hearing aid appraisal and selection may be operated solely by a user where software is contained on a designated storage medium and run on a single computing device or may be facilitated through a web-based interface where software will be stored on a remote server and accessed by clients worldwide using the internet or other remote communication network.

Figure 2:
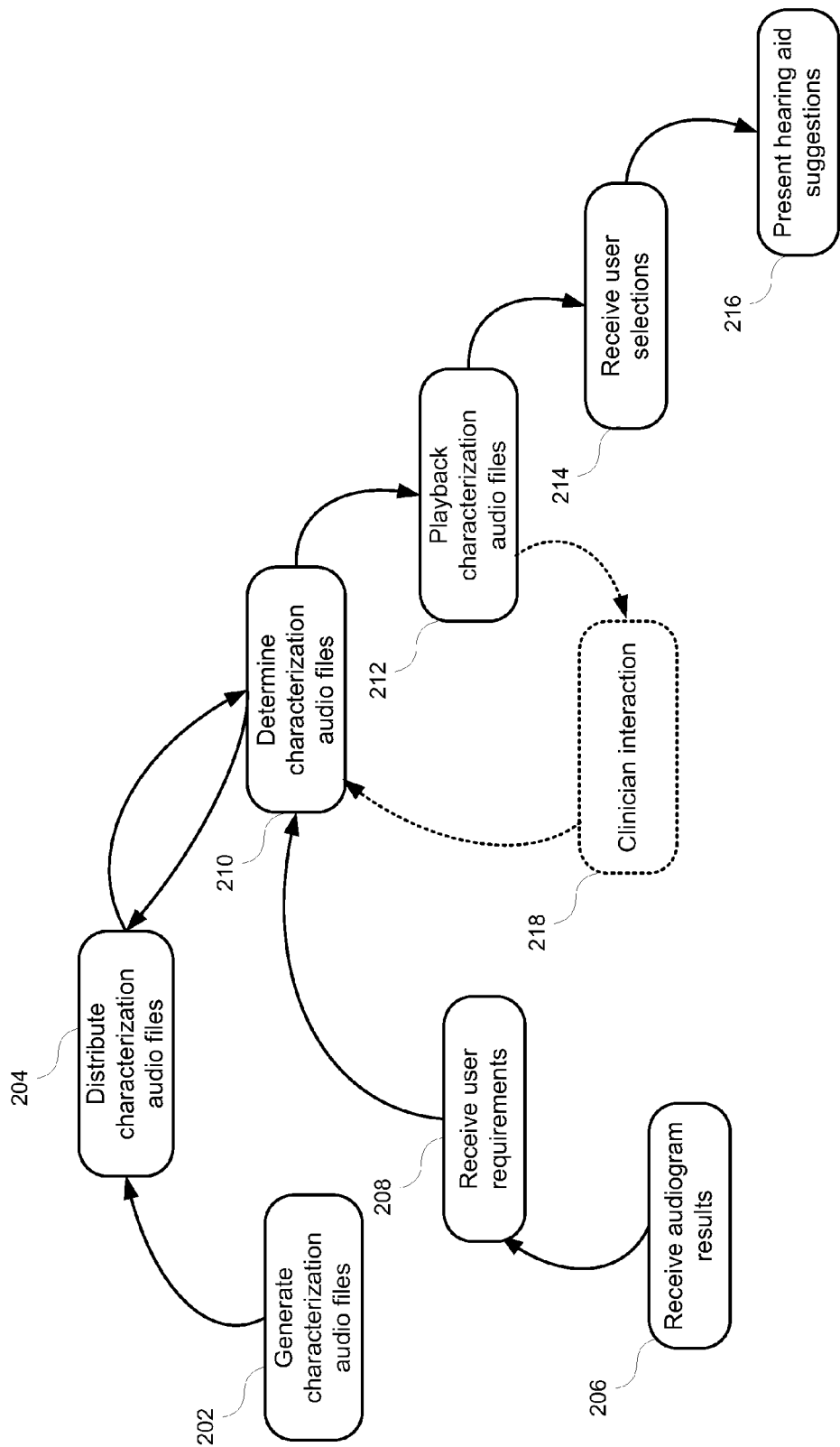
FIG. 2 shows a representation a process flow of hearing aid appraisal and selection.

FIG. 2 shows a representation a process flow of hearing aid appraisal and selection. The process commences with characterization audio files (202) being generated for each of the physical hearing aid. The characterization audio files are generated relative to one or more source sample files for varying parameters for the hearing aid. The characterization files, and associated configuration parameter files, or metadata, can be distributed (204) to computing devices utilized for user evaluation of the characterization files. The files may be distributed by a download process, or provided on-demand as part of the user interaction with the computing device (210), either by the computing device determining which characterization audio file are required and requesting them from the server, or by providing the server with user parameters enabling the server to select the appropriate files. In order to determine which types and configuration of hearing aids may be suitable for a user, an audiogram defining the hearing ability must be obtained to determine hearing loss of a user. The user parameters generated from audiometric results of the audiogram (206) may be provided via input by a clinician, by a hearing test performed on the computing device, or by entry of the parameters by the user into the computing device. User requirements such as lifestyle, cost, and expected level of benefit and aesthetic properties of the hearing aids can also be provided or entered by the user (208). From the user parameters and the user requirements a subset of hearing aids can be selected and the associated characterization audio files determined (210). The selection of the suitable hearing aid may be performed on the computing device, through interaction with a server such as the characterization server, or interaction with a networked server, such as a web server hosting the appraisal and selection process functionality. The characterization audio files can then be presented for playback (212) to the user, through the graphical user interface. The user may also interact with a clinician through an communication interface to enable the clinician to guide the process or determine appropriate audio files if required (218), The user can then hear the characterization files either individually or in defined sequences via a calibrated pair of audio transducers and make selections (214) based upon their preferences of the sound quality. From the selection preference of the user, suggestions of the most appropriate hearing aids for the user can be identified (216). The user can then have the identified hearing aids fitted.

Figure 3:
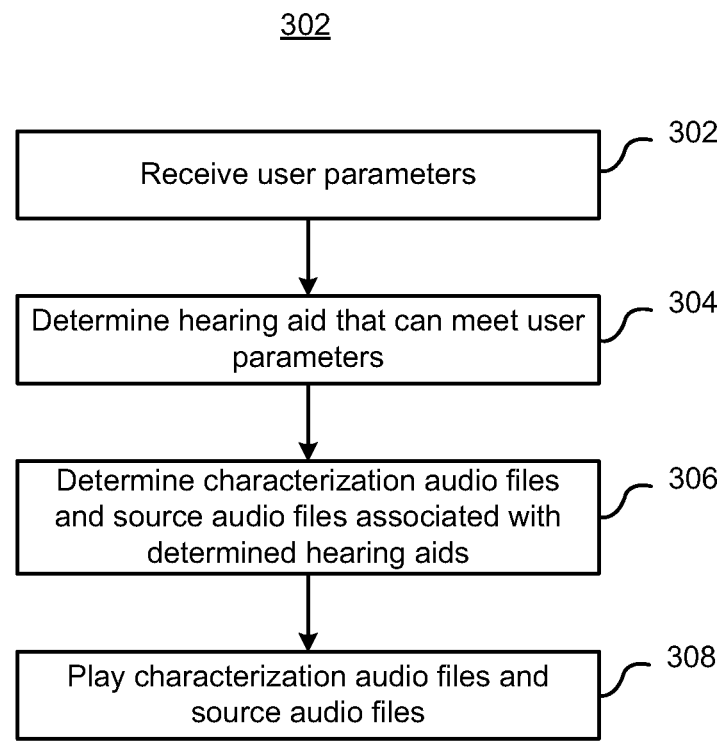
FIG. 3 shows a method of hearing aid appraisal and selection.

FIG. 3 shows a method 300 of hearing aid appraisal and selection. A plurality of user parameters determined for a user, such as derived from audiometric results of an audiogram defining the hearing ability of the user, is received (302) at a computing device. The user parameters may be input into the computing device or the parameters may be retrieved from a server where user information is maintained. Hearing aids that are configurable to meet the requirements of the plurality of configuration parameters are determined (304). The hearing aid may have configuration parameters such as prescribed gain, compression and/or any processing feature or which can be activated within the hearing aid(s) by way of its programming software and which can be modified to change the output of the hearing aid device. Characterization audio files associated with the determined hearing aid and an associated source audio file are determined (306) that best match the configuration parameters. The audio files may be stored on the computing device or retrieved via a network. The characterization audio files can then be played to the user through a playback device (308), such as headphone type audio transducers. The user can then compare the improvement in audio performance between the source file and the characterization audio files and make a selection of a preferred characterization audio file. The associated hearing aid can then be determined and identified in the graphical user interface, or provided to a clinician.

Figure 4:
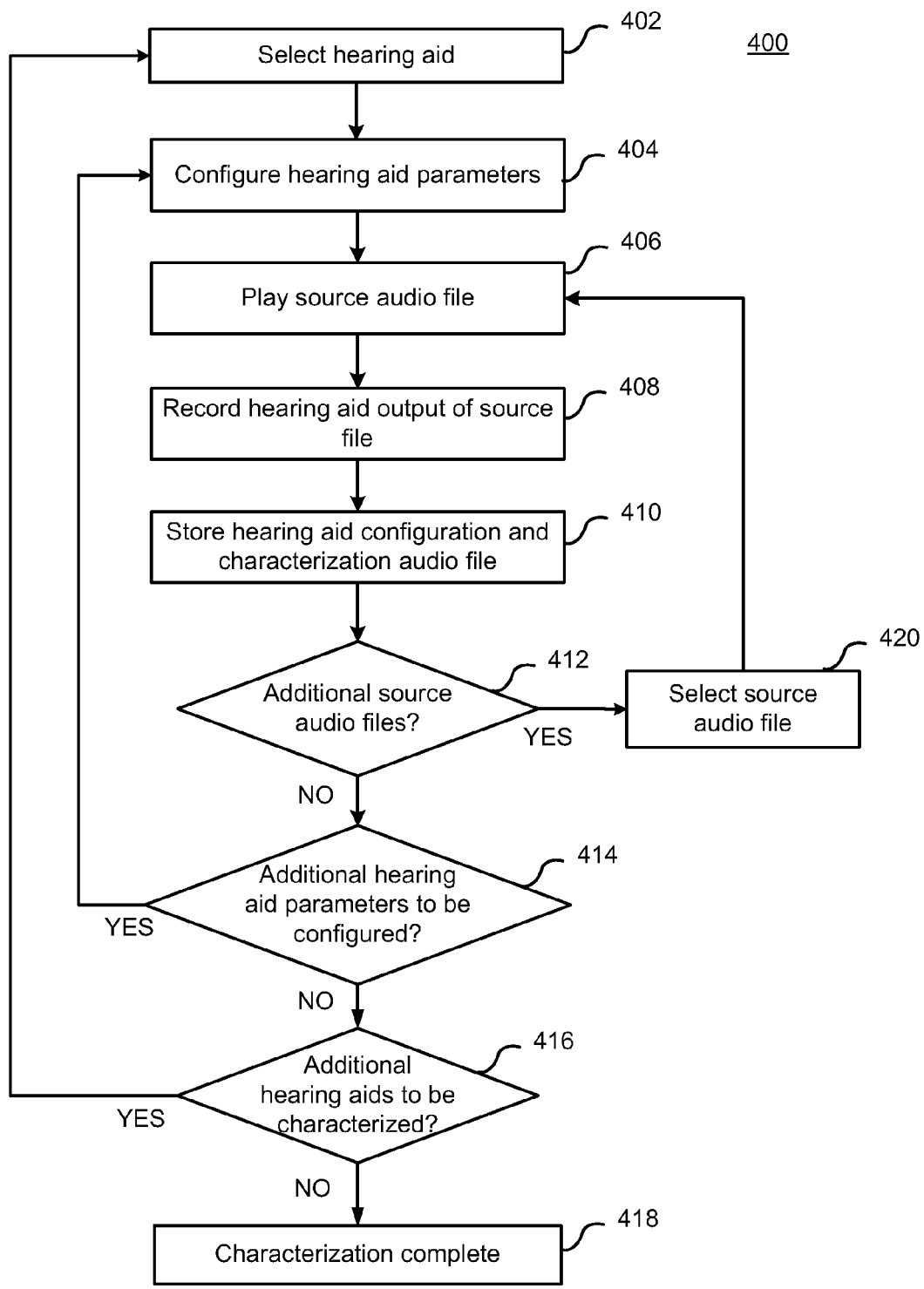
FIG. 4 shows a method of generating hearing aid characterization audio files.

FIG. 4 shows a method 400 of generating hearing aid characterization audio files. The hearing aid(s) to be characterized is selected (402). The hearing aid(s) is configured using programmable parameters of the hearing aid(s) (404) which may be performed by a communication interface with the hearing aid enabling software programming of the hearing aid parameters. A source audio file is played (406) through an loud speaker coupled to the input of the hearing aid(s) in a controlled environment. The output of the hearing aid is then recorded (408) and associated with an unprocessed source audio file and the configuration parameters which can then be stored (410). If there are additional source files to be characterized using the same configuration parameters by the hearing aid (YES at 412), they are selected (414) and played back for recording (406). If there are no additional source files to be characterized by the hearing aid for the particular configuration, but if there are additional hearing aid parameters to be configured for the particular device (YES at 414) the hearing aid is configured (404) and the source file is playback. It is assumed that a characterization audio file will be create for each common combination of hearing aid configuration, such as prescribed gain, compression and any processing feature or which can be activated within the hearing aid(s) by way of its programming software. If there are no additional configuration parameters (NO at 414), it is determined if there are additional hearing aid settings or parameters that require characterization. If there are additional hearing aids (YES at 416) the appropriate hearing aid is selected and the process recommences (402). If there are no additional hearing aids to be tested (NO at 416) the characterization is complete (418). The characterization audio file and hearing aid parameters can then be stored or up-loaded to computing devices for delivery of the appraisal and selection process. Alternatively, depending on the configurability of the hearing aid the method may be modified to allow for the hearing aid to be re-configured between playback of the same audio file, so that the configuration parameters of the hearing aid are cycled through prior to selection of another source file for playback.

Figure 5:
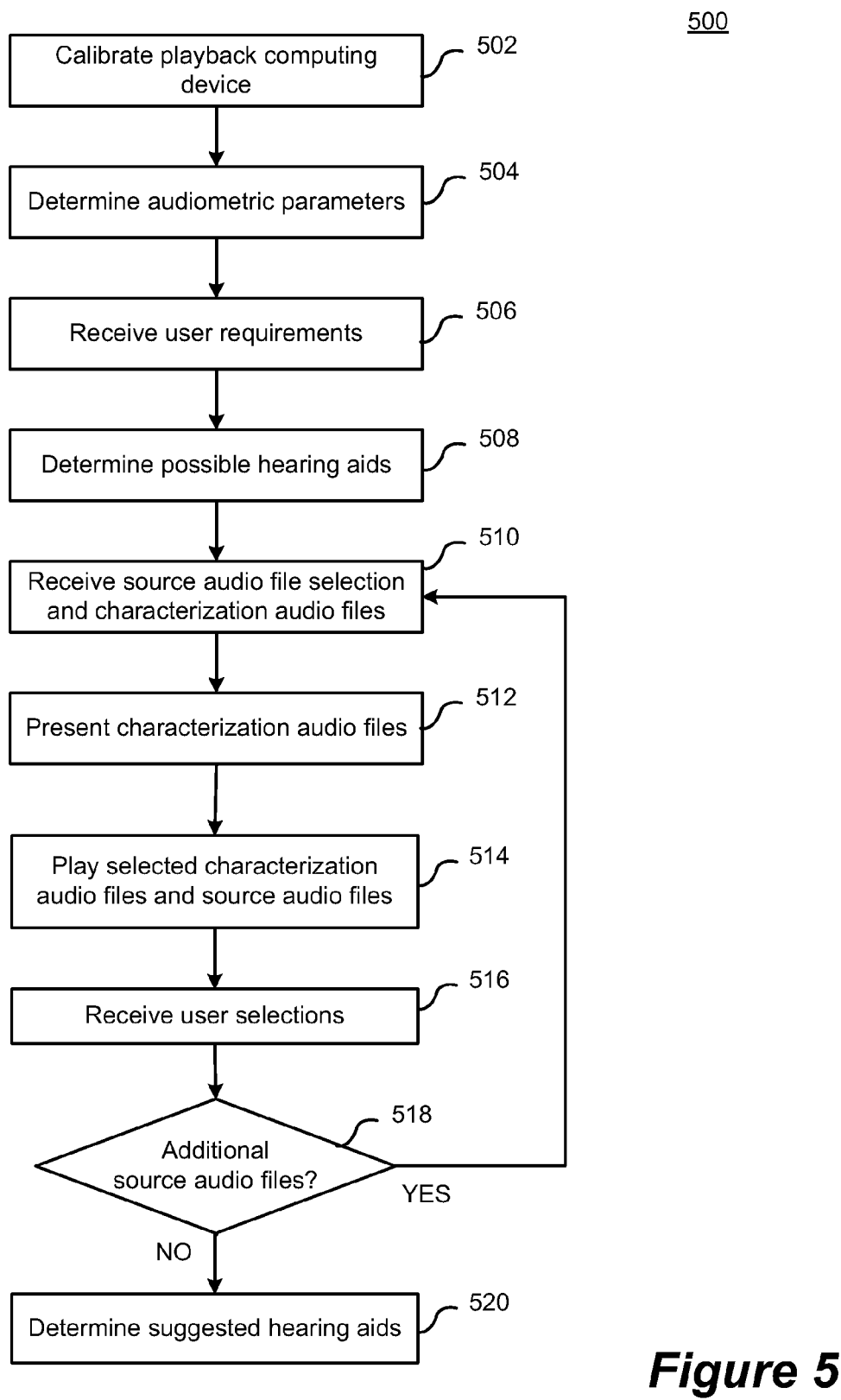
FIG. 5 shows a method of hearing aid appraisal and selection by a user.

FIG. 5 shows a method 500 of hearing aid appraisal and selection by a user. The playback computing device is calibrated to compensate for the audio processing chain and the audio transducers coupled to the computing device in order to provide an accurate estimation of the recording conditions of the characterization audio file. Audiogram parameters associated with a user defining the hearing-ability are determined (504), either through entry into the graphical user interface of an appraisal and selection application, or by retrieval from a storage location. User requirements can then be received (506), either by user entry or by retrieval. The user requirements may comprise aspects such as lifestyle, cost, expected level of benefit and aesthetic properties of the hearing aids. The lifestyle requirements could be defined relative to levels such as sedentary, active, or very active. The cost could be defined by levels such as entry, mid or high. The benefit could be associated with correction of quiet, correction of quiet and low level noise, correction in quiet and complex noise and correction for music. The aesthetic properties could be associated with a completely-in-the-earcanal hearing aid, an in-the-ear hearing aid, a behind-the-ear-hearing aid, or an implantable hearing aid. Each of these aspects can also be identified as part of the hearing aid specification which may be stored with the configuration parameters, for example a hearing aid may be identified as a small hearing aid for active people, mid-priced and provide benefit quite and complex noise. From the user parameters and user requirements specific hearing aids that may meet those requirements can be determined (508). The appropriate hearing aids can be determined by configuration parameters available to the device and specification identification associated with each device which are aligned with user requirements. The user may then select a source file (510) or a predefined sequence of source files. The associated characterization files may then be presented in the graphical user interface (512). Depending on the hearing ability of the user, each hearing aid may need to be uniquely configured for each ear. For example hearing loss may be more acute in one ear as opposed to the other. Therefore, separate characterization audio files may be selected for each ear and played simultaneously for the same source audio file. Depending on the number of determined hearing aids which meet the requirements, the characterization audio files may be presented in a sequential format. The characterization audio files may be presented in a detailed format identifying hearing aids being played, or the actual hearing aids may be presented in a blind testing format. The characterization audio files can then be played by user selection or in an automated sequence (514) or may be guided based upon user requirements. For example the user may only be looking for improved speech under certain noise conditions. The source audio file may also be presented to provide direct comparison to the characterization audio files. The user can then identify selections relative to the source audio file. The characterization audio files may also be presented relative to a variability of audiogram parameters and user requirements. For example, variations in prescribed gain or sound processing settings may be different for the same hearing aid device, and the same source file may be presented. If additional source audio files are selected by the user (YES at 518), or determined in a structured testing format, are retrieved and the playback process continues (510). If no additional configuration files are required for playback (NO at 518) the selected, or preferred, hearing aids can be identified, alternatively depending on the testing method the most preferable selection of hearing aids may be presented to the user, or provided to a clinician. At anytime during the playback process preferred selections may be identified and may not require all the selected or determined characterization audio files to be played. If multiple hearing aids have been identified as possibly meeting user requirements, the characterization audio files may be presented sequentially in an A/B format for each combination of hearing aids, possible multiple times, until a clear preference is determined. In a blind testing format the characterization audio files may be played without identification of the hearing aids themselves to remove selection bias that may occur if information is provided.

Figure 6:
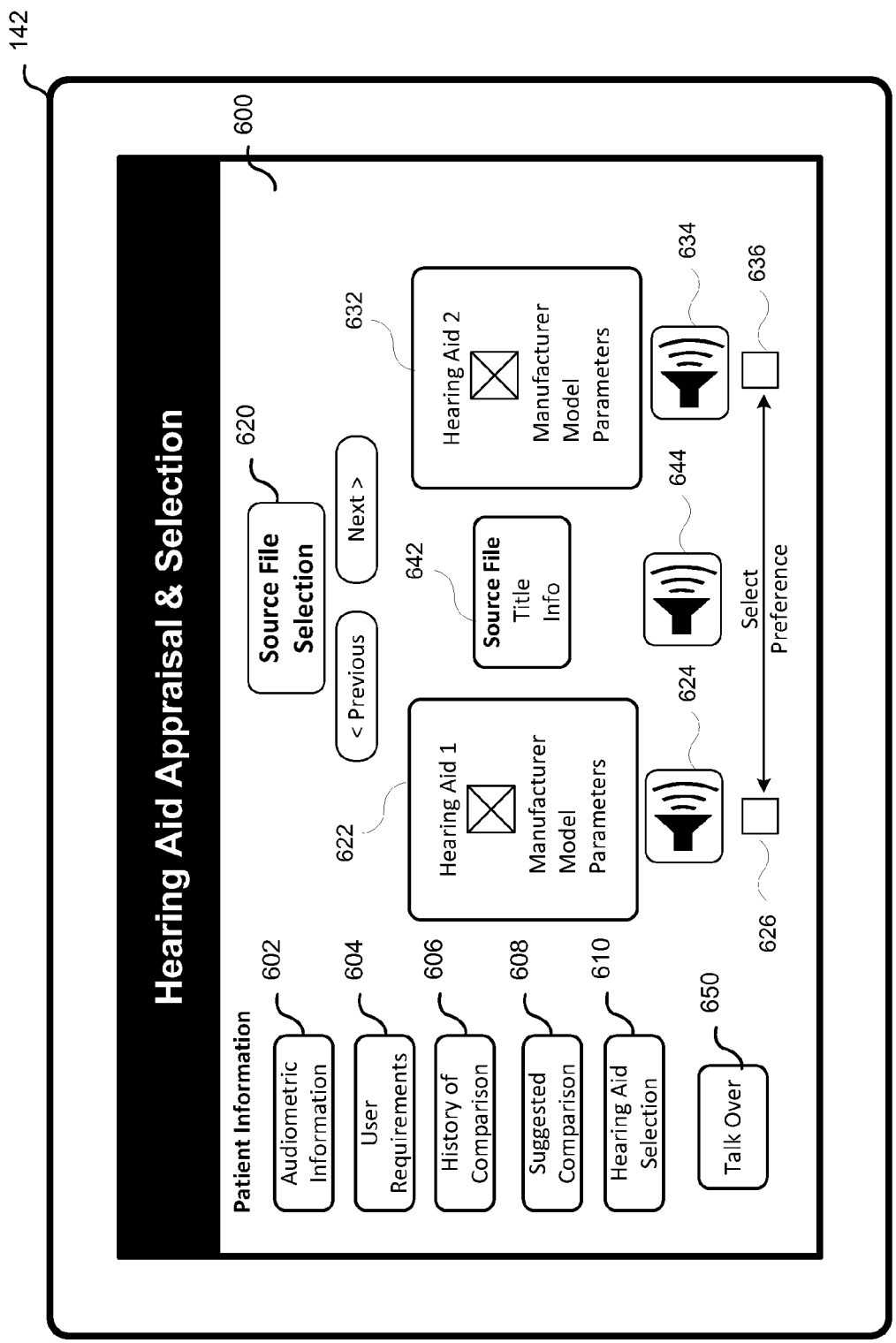
FIG. 6 shows a graphical user interface for hearing aid appraisal and selection.

FIG. 6 shows a graphical user interface for hearing aid appraisal and selection. The graphical user interface may be implemented in a computing device 142 in varying form factors, such as a tablet computer, smartphone, net book or desktop computer. The graphical user interface 600 may be provided through a web application or an installed or downloadable application on the computing device 142. The graphical user interface provided is a representation of an embodiment of the interface and different configurations, screen, layouts, buttons, interactive elements, menus or subscreen may be provided. Audiometric information 602 and user requirements 604 may be entered or reviewed through selection of audiometric information screen. The information may be stored at or retrieved from a server coupled to a network. A history log 606 may be provided to show the hearing aids previously selected and source files which were utilized in the hearing aid comparison process or identify progress through a testing sequence. In addition, suggested hearing aid comparisons 608 may be provided based upon the user parameters and requirements to enable the user to select specific hearing aids to hear. The user may also be able to select hearing aids for comparison that have not been determined as meeting the user parameters or user requirements but may potentially meet some of the requirements, for example a hearing aid outside of a particular price range may be better suited to a user and may not be part of the selection process but the user may choose to try the characterization audio files. Hearing aid selection 610 that have been made may also be selected. A selection menu 620 may be presented to select different source files and their associated characterization audio files. A menu listing the available audio files may be presented by which the user may select audio files, or be guided through specific audio files. In the comparison interface, information related to the selected, or suggested hearing aids 622 and 632, or to a source file, may be present in a graphical or textural representation of the hearing aid when one is selected. Depending on the configuration of the application details of the particular hearing aid may be presented, such as an image of the hearing aid, manufacturer, model, parameters or input conditions that are associated with the hearing aid. Alternatively the particular hearing aid information may not be provided to not bias user selection and provide a blind testing format or may not be presented if two different characterization audio files are being played, one for each ear of the user if the hearing ability is different for each ear. Identification of the sample file 642 may also be provided for reference and enable playback for comparison to enable the user to see the improvement. A respective playback button 624, 634, and 644 may be provided with a selection preference indicator 626 and 636 to allow a user to identify which hearing aid they preferred. The user interface may be simplified depending on the implementation or may present additional information if used in a clinical environment. A talk over button 650 may be provided to enable interaction with a clinician which may monitor the progress of the user. The talk over button 650 may be provided when a separate pair of monitoring headphones and microphone is coupled to the computing allowing the clinician to directly communicate with the patient. Alternatively the talk over button may be provided in the user interface presented to the clinician on a computing device separate from the user's computing device to enable remote interaction. The clinician may also guide the selection of source file to the user based upon interaction with the user or based upon results received during the appraisal process.

Although certain methods, apparatus, computer readable memory, and articles of manufacture have been described herein, the scope of coverage of this disclosure is not limited thereto. To the contrary, this disclosure covers all methods, apparatus, computer readable memory, and articles of manufacture fairly falling within the scope of the appended claims either literally or under the doctrine of equivalents.

Although the following discloses example methods, system and apparatus including, among other components, software executed on hardware, it should be noted that such methods, system and apparatus are merely illustrative and should not be considered as limiting. For example, it is contemplated that any or all of these hardware and software components could be embodied exclusively in hardware, exclusively in software, exclusively in firmware, or in any combination of hardware, software, and/or firmware. Accordingly, while the following describes example methods and apparatus, persons having ordinary skill in the art will readily appreciate that the examples provided are not the only way to implement such methods, system and apparatus.

The invention claimed is:

1. A method, executable on one or more processors, of appraisal and selection of hearing aids, the method comprising:

receiving a plurality of user parameters determined from audiometric parameters defining hear-ability of the user;

determining one or more hearing aids, configurable to meet the requirements of the plurality of user parameters;

determining one or more pre-recorded characterization audio files each associated with one of the determined one or more hearing aids, the pre-recorded characterization audio files having been generated by recording an output from a respective hearing aid of a source file played through the respective hearing aid configured using a set of configuration parameters to meet the requirements of the plurality of user parameters and determining associated source audio files from which the one or more pre-recorded characterization audio files were generated; and playing to the user through audio transducers coupled to a playback device the one or more pre-recorded characterization audio files and the associated source audio files to simulate the determined one or more hearing aids.

2. The method of claim 1 further comprising determining one or more source files based upon the plurality of received user parameters prior to determining the one or more pre-recorded characterization audio files.

3. The method of claim 2 further comprising receiving a user selection of a source audio file from the determined one or more source files.

4. The method of claim 1 wherein determining the one or more pre-recorded characterization audio files is performed for user parameters defined for each ear of the user, wherein a different pre-recorded characterization audio file is played to each ear of the user simultaneously.

5. The method of claim 1 further comprises receiving an indication of a user's preference of the one or more pre-recorded characterization audio files of an associated hearing aid.

6. The method of claim 1 wherein the plurality of user parameters further comprises user requirements used for determining the selection of the determined one or more hearing aids configurable to meet the requirements of the plurality of user parameters.

7. The method of claim 1 wherein the one or more hearing aids is determined to meet the requirements of the plurality of user parameters, the method further comprising:
receiving indication of a preference of one or more of the pre-recorded characterization audio files; and
providing identification of the one or more hearing aids associated with the one or more pre-recorded characterization audio files indicated as preferable.

8. The method of claim 1 wherein determining the one or more hearing aids configurable to meet the requirements of the plurality of user parameters comprises mapping the user parameters to configuration parameters identified for each of the plurality of pre-recorded characterization audio files.

9. The method of claim 1 wherein the plurality of pre-recorded characterization audio files is presented in a blind testing format in a graphical user interface.

10. The method of claim 1 further comprising providing audio interaction by a clinician during playback of the pre-recorded characterization audio files to provide context or instruction to the user of the playback device.

11. A system of appraisal and selection of hearing aids, the system comprising:
audio transducers; and
a computing device coupled to the audio transducers, the computing device performing:
receiving a plurality of pre-recorded characterization audio files each generated by recording an output from a respective hearing aid of a source file played through the respective hearing aid having been configured using a set of configuration parameters, the plurality of characterization audio files selected by determining one or more hearing aids configurable to meet the requirements of a plurality of user parameters defining hear-ability of the user and the respective pre-recorded characterization audio files generated using the plurality of user parameters defining the hear-ability of the user;
playing to the user, through the audio transducers, each of the plurality of pre-recorded characterization audio files and associated source audio files to simulate the determined one or more hearing aids; and
receiving a preference selection of one or more of the plurality of pre-recorded characterization audio files to identify a hearing aid preference.

12. The system of claim 11 wherein the computing device further performs:
receiving a plurality of user parameters determined from audiometric parameters defining hear-ability of the user; and
determining the plurality of pre-recorded characterization audio files to be provided for playback to the user by determining hearing aids which meet the received plurality of user parameters.

13. The system of claim 12 further comprising a computing device comprising a loudspeaker;
a microphone; and
a characterization server coupled to the loudspeaker and microphone, the characterization server for playing the source file through the loudspeaker to the respective hearing aid and for recording an associated characterization audio file from the microphone to be stored for retrieval by the computing device.

14. The system of claim 13 wherein the respective hearing aid is configured using a plurality of configuration parameters programmed through a wired or wireless connection to the respective hearing aid and a plurality of configuration parameters are associated with the pre-recorded characterization audio file.

15. The system of claim 11 wherein the characterization server determines the plurality of pre-recorded characterization audio files to be provided for playback to the user by determining hearing aids which meet the received plurality of user parameters and provides the plurality of characterization audio files to the computing device.

16. The system of claim 11 further comprising determining hearing aids configurable to meet the requirements of the plurality of user parameters by matching the user parameters to configuration parameters identified for the plurality of hearing aids and the associated plurality of pre-recorded characterization audio files.

17. The system of claim 11 wherein the computing device uses a calibration configuration to provide a desired audio level output by the audio transducers.

18. The system of claim 11 wherein a pair of characterization audio files is played simultaneously, one for each ear of the audio transducers, the pair of pre-recorded characterization audio files associated with a common source audio files.

19. The system of claim 11 wherein the computing device further comprises headphones and a microphone to enable communication between a user and an operator to provide verbal communication there between.

20. A non-transitory computer readable memory containing instructions which when executed on one or more processor for providing appraisal and selection of hearing aids, the instructions comprising:
receiving a plurality of user parameters determined from audiometric parameters defining hear-ability of the user;
determining one or more hearing aids, configurable to meet the requirements of the plurality of user parameters;
determining one or more pre-recorded characterization audio files each associated with one of the determined one or more hearing aids, the pre-recorded characterization audio files having been generated by recording an output from a respective hearing aid of a source file played through the respective hearing aid having been configured using a set of configuration parameters to meet the requirements of the plurality of user parameters and associated source audio files from which the one or more pre-recorded characterization audio files were generated; and playing to the user through audio transducers coupled to a playback device the one or more pre-recorded characterization audio files and the associated source audio files to simulate the determined one or more hearing aids.

\* \* \* \* \*